(12) United States Patent
Sugaya et al.

(10) Patent No.: US 7,435,382 B2
(45) Date of Patent: Oct. 14, 2008

(54) INCUBATOR

(75) Inventors: Fumio Sugaya, Kanagawa-ken (JP); Akihiro Komatsu, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 873 days.

(21) Appl. No.: 10/993,482

(22) Filed: Nov. 22, 2004

(65) Prior Publication Data
US 2005/0089445 A1    Apr. 28, 2005

Related U.S. Application Data

(62) Division of application No. 10/042,319, filed on Jan. 11, 2002, now abandoned.

(30) Foreign Application Priority Data

Jan. 11, 2001  (JP) .............................. 2001-003179
Jan. 11, 2001  (JP) .............................. 2001-003181

(51) Int. Cl.
    *G01N 35/00* (2006.01)
(52) U.S. Cl. .............................. 422/64; 422/63; 436/43; 436/45
(58) Field of Classification Search ............. 422/63–64, 422/72; 236/2; 436/43, 45–46
    See application file for complete search history.

(56) References Cited

U.S. PATENT DOCUMENTS

| 4,823,169 A | 4/1989 | Ogura |
| 5,037,613 A | 8/1991 | Shaw et al. |
| 6,531,094 B2 * | 3/2003 | Seto et al. ...................... 422/64 |
| 7,285,245 B2 * | 10/2007 | Seto ............................. 422/65 |
| 2002/0090322 A1 * | 7/2002 | Sugaya et al. ................. 422/64 |
| 2002/0098117 A1 * | 7/2002 | Ammann et al. .............. 422/64 |
| 2002/0114733 A1 * | 8/2002 | Copeland et al. ............. 422/64 |
| 2003/0017613 A1 * | 1/2003 | Jakubowicz et al. ........ 436/174 |
| 2004/0191121 A1 * | 9/2004 | Tomasso et al. ............... 422/65 |

FOREIGN PATENT DOCUMENTS

| JP | 5-72976 | 3/1993 |
| JP | 11-237386 | 8/1999 |

* cited by examiner

*Primary Examiner*—Brian R. Gordon
(74) *Attorney, Agent, or Firm*—Sughrue Mion, PLLC (57) ABSTRACT

An incubator includes a rotating incubator rotor. The incubator rotor is provided with a plurality of element chambers which are arranged along the outer periphery of the incubator rotor and each of which accommodates a dry analysis element spotted with a sample and incubates the dry analysis element. A light measuring system has a light measuring head which measures the optical density of the dry analysis element. The light measuring system is provided with a correction system which compensates for fluctuation in the value of the optical density of the dry analysis element in each of the element chambers as measured by the light measuring head generated due to fluctuation in the distance between the light measuring head and the element chamber on the basis of a correction value which has been stored in the correction system element chamber by element chamber.

2 Claims, 6 Drawing Sheets

FIG.6 ately analyze the concentration of a
INCUBATOR

This is a divisional of application Ser. No. 10/042,319 filed Jan. 11, 2002 now abandoned.

BACKGROUND OF THE INVENTION

1. Field of the Invention

This invention relates to an incubator which is used in a biochemical analysis system, in which a sample such as blood or urine is spotted onto a dry analysis element and, for instance, the concentration of a specific biochemical component contained in the sample is detected, to keep the dry analysis element at a constant temperature in order to measure change of the optical density.

2. Description of the Related Art

Recently, there has been put into practice a colorimetric dry (dry-to-the touch) analysis element with which the content of a specific biochemical component or a specific solid component contained in a sample liquid can be quantitatively analyzed by simply spotting a droplet of the sample liquid. Since being capable of analyzing samples easily and quickly, the biochemical analysis systems using such dry analysis elements are suitably used in medical institutions, laboratories and the like.

When quantitatively analyzing the chemical components or the like contained in a sample liquid using such a colorimetric dry analysis element, a droplet of the sample liquid is spotted on the analysis element, and the analysis element is held at a constant temperature for a predetermined time in an incubator so that a coloring reaction (pigment forming reaction) occurs, and the optical density of the color formed by the coloring reaction is optically measured. That is, measuring light containing a wavelength which is pre-selected according to the combination of the component to be analyzed and the reagent contained in the analysis element is projected onto the analysis element and the optical density of the analysis element is measured. Then the concentration of the component to be analyzed is determined on the basis of the optical density according to a calibration curve representing the relation between the concentration of the specific biochemical component and the optical density.

Figure 4:
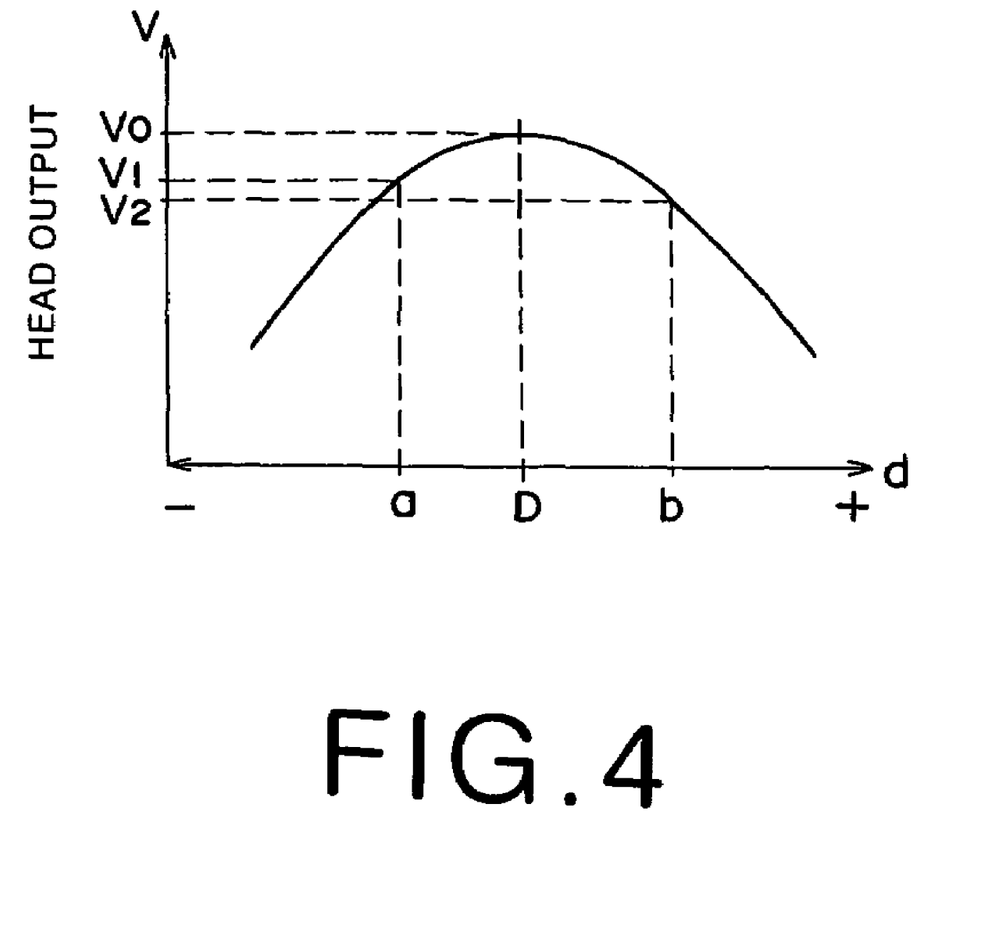
FIG. 4 is a view for illustrating change of the sensitivity of the light measuring head with the distance between the element chamber and the light measuring head.

When the distance between the dry analysis element and the light measuring head (a head for projecting said measuring light onto the dry analysis element and receives light from the dry analysis element bearing thereon the optical density of the dry analysis element fluctuates, there can be produced measuring errors since the light measuring head has own optimal measuring distance due to its light measuring sensitivity properties as will be described later in conjunction with FIG. 4. In order to accur specific component in the sample, it is necessary to detect even a slight coloring reaction and it is required for the colorimetry to be carried out at a high accuracy. Accordingly, it is important to keep constant the distance between the dry analysis element and the light measuring head.

In Japanese Patent Publication No. 5(1993)-72976, the optical components of the light measuring head are positioned where the output of the light measuring head is maximized, so that the influence of variation of the distance on the light measuring sensitivity is minimized.

In U.S. Pat. No. 5,037,613, there is disclosed a structure in which the lower surface of the outer periphery of the incubator rotor, which is rotated with dry analysis elements spotted with the samples accommodated therein, is supported by a sliding support so that the rotational displacement of the incubator rotor is suppressed and the distance between the light measuring head and each of the dry analysis elements arranged along the outer periphery of the incubator rotor is held constant.

However, the approach disclosed in the aforesaid Japanese patent publication is disadvantageous in that though fluctuation of the distance can be held in an acceptable range where the influence of variation of the distance on the light measuring sensitivity can be suppressed by the arrangement of the optical components so long as the diameter of the incubator rotor is small and the rotational displacement of the incubator rotor is small, fluctuation of the distance becomes too large for the optical components to suppress the influence of variation of the distance on the light measuring sensitivity in an acceptable range when the number of the dry analysis elements to be accommodated in the incubator increases and the diameter of the incubator rotor increases. An attempt to limit the rotational displacement of a large incubator rotor increases requirement on processing accuracy and fabricating accuracy of the components of the incubator rotor, thereby adding to the manufacturing cost of the incubator.

The approach disclosed in the United states patent is disadvantageous in that as the sliding support wears, the rotational displacement of the incubator rotor increases and the incubator rotor drive mechanism can become unstable due to nonuniform load and wear of the sliding support will produce dust.

Displacement in height of the incubator rotor relative to the measuring head during rotation of the incubator rotor is generated by strain generated when forming the rotor and/or strain generated when mounting the rotor on the rotating shaft. Accordingly, the distance between the measuring head and each of the element chambers arranged along the outer periphery of the incubator rotor when the element chamber is brought to a predetermined position, e.g., a light measuring position where the optical density of the dry analysis element is to be measured, is constant for each element chamber but differs from chamber to chamber. As the difference in the distance between the measuring head and the element chambers increases, variation in the measured value for a given optical density becomes larger.

As disclosed, for instance, in Japanese Unexamined Patent Publication No. 11(1999)-237386, there has been known an incubator provided at its center with an element discarding hole through which dry analysis elements after measurement are discarded by pushing the dry analysis elements further inward by the element transfer member which pushes the dry analysis elements into the element chambers of the incubator. This structure is advantageous in that the dry analysis elements can be easily discarded with the transfer mechanism of a simple structure.

However, as the number of the dry analysis elements to be accommodated in the incubator increases and the diameter of the incubator rotor increases, the diameter of the discarding hole must be large in order to discard the dry analysis elements in all the element chambers by a limited stroke of the element transfer member. When the diameter of the discarding hole is enlarged and the diameter of the rotating shaft of the incubator rotor is increased, the diameter of the bearing member for supporting the rotating shaft must be large, which adds to the manufacturing cost of the bearing member. Especially when the bearing member must support the rotating shaft of the incubator rotor so as to suppress the rotational displacement of the incubator rotor in the acceptable range as described above, the manufacturing cost of the bearing member is further increased.

On the other hand, when the diameter of the element discarding hole is reduced, the distance over which the dry analysis elements are conveyed to be discarded becomes longer, which adds to the length and stroke of the element transfer member and increases the overall size and weight of the apparatus.

SUMMARY OF THE INVENTION

In view of the foregoing observations and description, the primary object of the present invention is to provide an incubator which can accurately measure the optical density of the dry analysis element in all the element chambers of the incubator without using a sliding support and can be manufactured at low cost even if it is provided with a large number of element chambers and is large in size.

Another object of the present invention is to provide an incubator which is precise in rotation and small in weight and in which the dry analysis elements can be easily discarded after measurement.

The first object of the present invention can be accomplished by an incubator comprising a rotating incubator rotor provided with a plurality of element chambers which are arranged along the outer periphery of the incubator rotor and each of which accommodates a dry analysis element spotted with a sample and incubates the dry analysis element and a light measuring means having a light measuring head which measures the optical density of the dry analysis element, wherein the improvement comprises that the light measuring means is provided with a correction means which compensates for fluctuation in the value of the optical density of the dry analysis element in each of the element chambers as measured by the light measuring head generated due to fluctuation in the distance between the light measuring head and the element chamber on the basis of a correction value which has been stored in the correction means element chamber by element chamber.

It is preferred that the correction means sets the correction value for each element chamber by inserting a calibration element whose optical density is known into each of the element chambers of the incubator rotor, measuring the optical density of the calibration element with the light measuring head and determining the correction value for the element chamber on the basis of the difference between the known optical density of the calibration element and the measured optical density of the same.

In the incubator of this invention, since the measured value of the optical density of the dry analysis element in each element chamber is corrected on the basis of a correction value which is set according to the position of the element chamber, i.e., the distance between the light measuring head and the element chamber in which the dry analysis element is accommodated, the optical density can be accurately measured for each element chamber even if the distance between the light measuring head and each of the element chambers of the incubator fluctuates chamber to chamber. Accordingly, the incubator rotor need not be so precisely manufactured and the sliding support becomes unnecessary, whereby the incubator can be easily manufactured at low cost and the durability of the incubator is increased.

When the correction means sets the correction value for each element chamber by inserting a calibration element whose optical density is known into each of the element chambers of the incubator rotor, measuring the optical density of the calibration element with the light measuring head and determining the correction value for the element chamber on the basis of the difference between the known optical density of the calibration element and the measured optical density of the same, setting of the correction value is facilitated.

That is, though the incubator rotors rotate in different ways according to the processing accuracy and the like and the distance between the light measuring head and each of the element chambers in the measuring position to which the element chambers are brought in sequence as the incubator rotor rotates differs element chamber to element chamber, the optical density can be accurately measured for each element chamber irrespective of fluctuation in distance between the light measuring head and the element chamber by correcting the measured value for each element chamber on the basis of a correction value determined for each element chamber according to the real distance between the light measuring head and the element chamber. The correction value for each element chamber can be easily set by reading the measurement for a calibration element whose optical density is known and determining the correction value on the basis of the difference between the known optical density and the measured value.

The second object of the present invention can be accomplished by an incubator comprising a rotating incubator rotor provided with a plurality of element chambers which are arranged along the outer periphery of the incubator rotor and each of which accommodates a dry analysis element spotted with a sample and incubates the dry analysis element, wherein the improvement comprises that the incubator rotor is provided with a cone-like slant surface which is formed below the element chambers and tapers downward toward the axis of rotation of the incubator rotor, a cylindrical rotating shaft which is connected to the lower end of the slant surface and the inner space of which opens to the space defined by the cone-like slant surface so that the dry analysis element in each element chamber can be discarded outside the incubator through the space defined by the cone-like slant surface and the inner space of the cylindrical rotating shaft and a bearing member which supports the cylindrical rotating shaft for rotation about the axis of rotation of the incubator rotor.

It is preferred that the slant surface be at an angle not smaller than 30° to the horizontal so that the dry analysis element is surely slid on the slant surface toward the cylindrical rotating shaft.

In the incubator of this arrangement, the rotating shaft need not be large in diameter even if the number of the dry analysis elements to be accommodated in the incubator increases and the diameter of the incubator rotor increases, and accordingly, the bearing member may be small in diameter, whereby the incubator can be manufactured at low cost. Further, since the dry analysis elements after measurement can be discarded by pushing the dry analysis elements only to the slant surface, the stroke of the element transfer member need not be enlarged even if the number of the dry analysis elements to be accommodated in the incubator increases and the diameter of the incubator rotor increases, whereby the incubator can be small in size and weight.

Further by virtue of the member defining the cone-like slant surface, rigidity of the incubator rotor is increased and the incubator rotor can be rigid enough though it is small in weight, whereby wobbling of the incubator rotor can be suppressed without use of a sliding support and the measuring accuracy can be enhanced.

The incubator can be employed to incubate various types of dry analysis element without limited to the calorimetric dry analysis element. For example, the incubator can be employed to incubate electrolytic dry analysis elements for measuring the activity of a specific ion contained in a sample liquid.

DESCRIPTION OF THE PREFERRED EMBODIMENT

Figure 1:
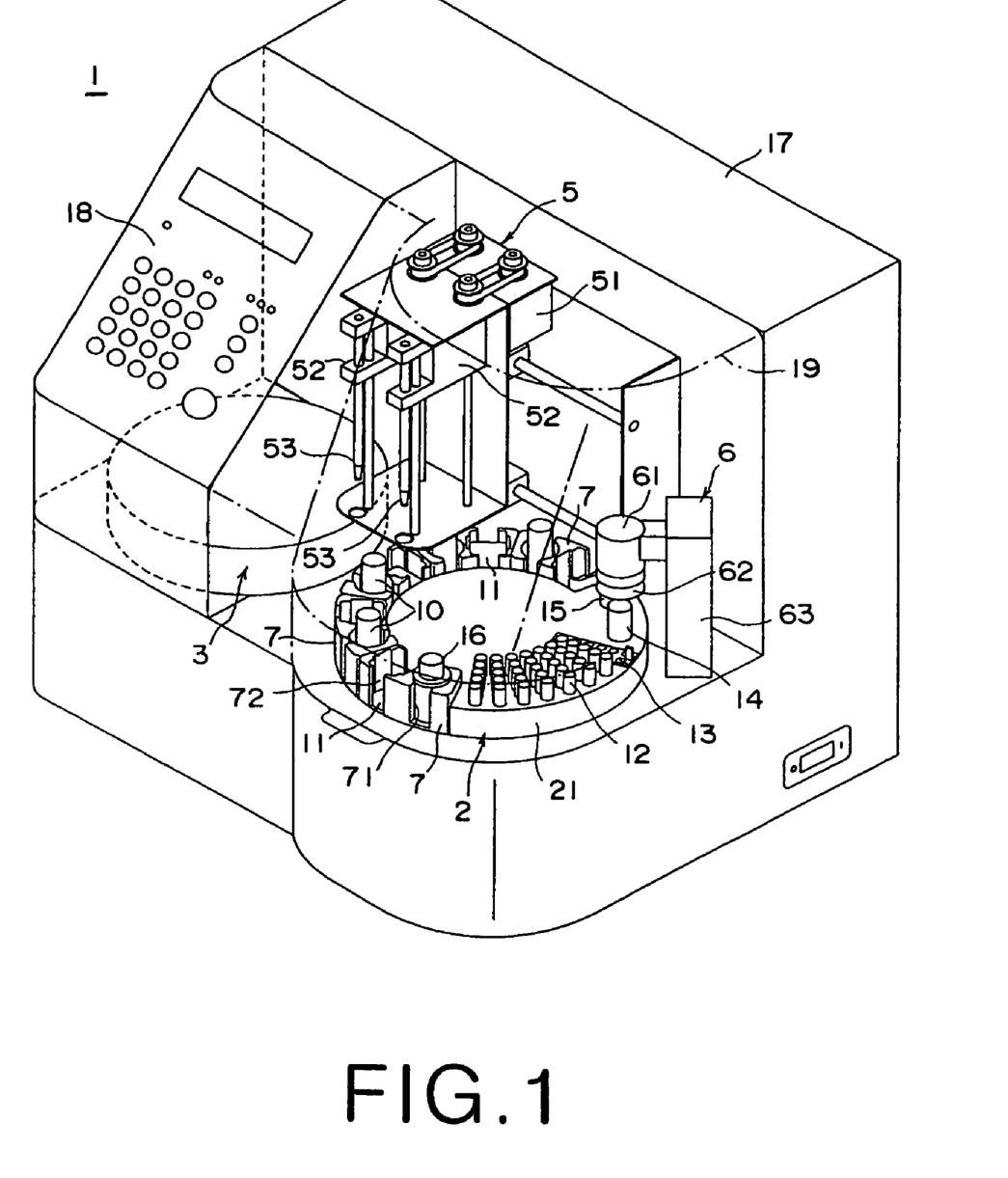
FIG. 1 is a perspective view showing a biochemical analysis system provided with an incubator in accordance with an embodiment of the present invention.

In FIG. 1, a biochemical analysis system 1 comprises a system body 17 and a circular sample tray 2 is provided on one side of the front portion of the system body 17. A circular incubator 3 is provided on the other side of the front portion of the system body 17, and a spotting station (not shown) is provided between the sample tray 2 and the incubator 3. Further a spotting nozzle unit 5 is provided on an upper portion of the system body 17 to be movable right and left. A dry analysis element 11 held in a sample cartridge 7 is moved to the spotting station and spotted with a sample. Then the dry analysis element 11 spotted with the sample is transferred to the incubator 3. A blood filtering unit 6 for separating blood plasma from blood is provided beside the sample tray 2.

Figure 2:
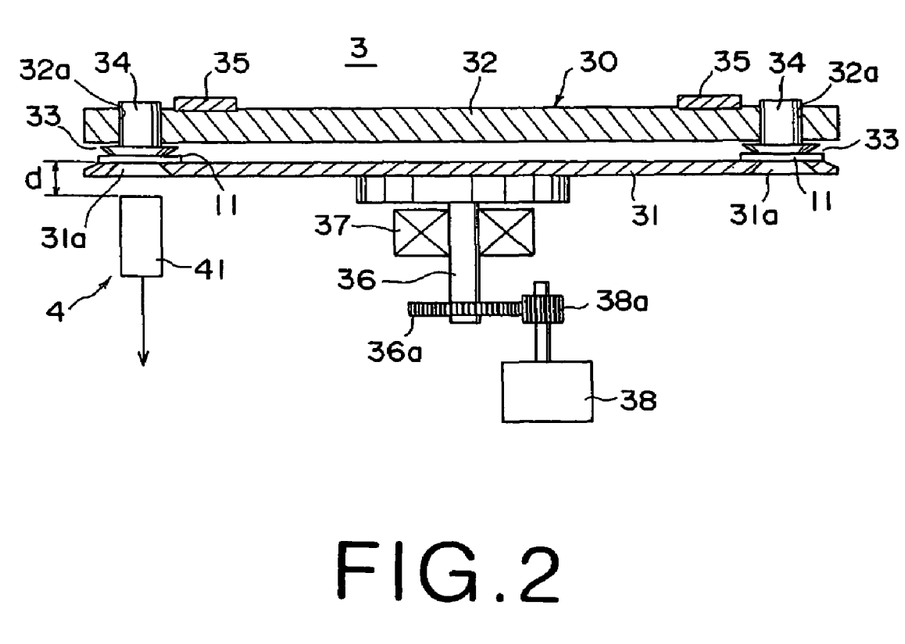
FIG. 2 is a schematic cross-sectional view showing the incubator with the cover removed.

The incubator 3 comprises an incubator rotor 30 and a measuring means 4. The incubator rotor 30 comprises lower and upper disc members 31 and 32, and a plurality of element chambers 33 in which the dry analysis elements 11 are inserted are formed between the lower and upper disc members 31 and 32 arranged along the circumference of the disc members 31 and 32 at regular intervals.

A rotating shaft 36 extends downward at the center of the lower disc member 31 and the rotating shaft 36 is supported for rotation by a bearing member 37 so that the lower disc member 31 is rotated horizontally about the rotating shaft 36. A sprocket 36s is fixed to the lower end portion of the rotating shaft 36 and in mesh with a drive gear 38a fixed to the output shaft of a drive motor 38 so that the incubator rotor 30 is rotated in the regular direction and the reverse direction by the drive motor 38.

Sliding holes 32a are formed in the upper disc member 32 to be opposed to the element chambers 33. A pressing member 34 is disposed above each element chamber 33 with its upper portion slidably received in the sliding hole 32a. The lower surface of the pressing member 34 presses downward the dry analysis element 11 inserted into the element chamber 33 and tightly closes the spotting hole of the dry analysis element 11 (through which the sample is spotted onto the element 11) to prevent evaporation thereof. The outer edge of the lower portion of the pressing member 34 is tapered so that the dry analysis element 11 inserted into the element chamber 33 is brought into abutment against the tapered surface to push upward the pressing member 34.

A heater 35 is provided in the upper disc member 32 to heat the dry analysis elements 11 in the element chambers 33. By controlling the heater 36, the dry analysis elements can be held at a desired constant temperature (incubated).

A light measuring window 31a is formed in the bottom of the lower disc member 31 opposed to each of the element chambers 33. A light measuring head 41 is positioned below the light measuring window 31a of the element chamber 33 stopped in a light measuring position shown in FIG. 2. Though not shown, the incubator rotor 30 is covered with a cover in order to cut influence of the ambient temperature to the dry analysis elements 11 and to prevent external light from impinging upon the light measuring head 41.

The incubator rotor 30 is rotated back and forth so that the element chambers 33 are brought to the light measuring position in sequence and returned to the initial position after measurement of the optical density of each dry analysis element 11 due to the coloring reaction.

When the optical density is measured, the light measuring head 41 projects measuring light containing a wavelength which is pre-selected according to the combination of the component to be analyzed and the reagent contained in the dry analysis element 11 onto the dry analysis element 11 through the light measuring window 31a and measures the optical density of the dry analysis element 11. The light measuring head 41 is mounted on the incubator body (not shown). As the incubator rotor 30 is rotated by the drive motor 30, the distance d between the element chamber in the light measuring position and the light measuring head 41 periodically changes since the height of the incubator rotor 30 in the light measuring position varies according to the angle at which the incubator rotor 30 is mounted on the rotating shaft 36.

Figure 3:
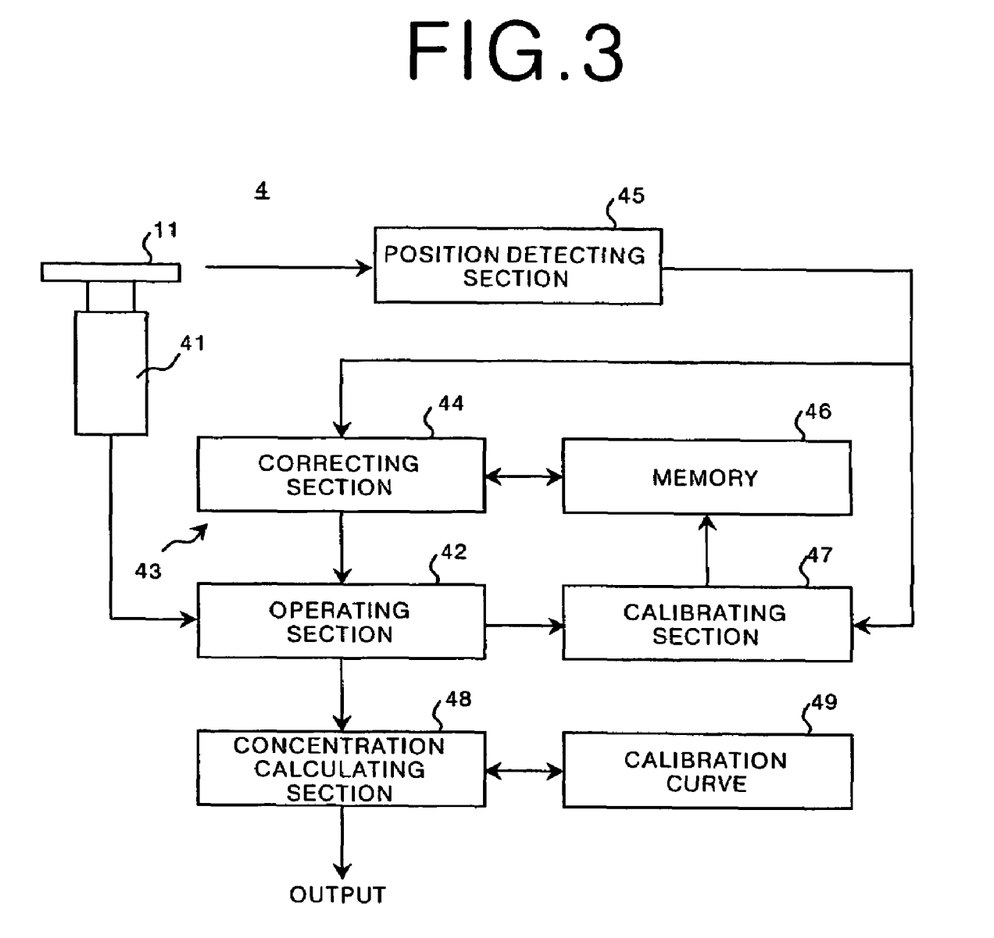
FIG. 3 is a block diagram showing the measuring mean.

As shown in FIG. 3, the optical density of the dry analysis element 11 as measured by the light measuring head 41 is sent to an operating section 42 and is corrected by a correction means 43 on the basis of a correction value which has been stored for the position of each element chamber 33 (for the distance of each element chamber 33 from the light measuring head 41 when the element chamber 33 is in the light measuring position). The correction means 43 is provided with a correcting section 44. The correcting section 44 receives a signal from a position detecting section 45 which represents the position of the element chamber 33 which is stopped above the light measuring head 41 (in the light measuring position) and reads out a correction value corresponding to the element chamber 33 stopped above the light measuring head 41 from a memory 46. The operating section 42 corrects the optical density of the dry analysis element 11 in the element chamber 33 in the light measuring position on the basis of the correction value, thereby obtaining a true optical density of the dry analysis element 11 free from influence of fluctuation in distance.

The position detecting section 45 detects the rotational phase of the incubator rotor 30 by way of rotation of the motor 38 (e.g., by the use of a rotary encoder) and detects the element chamber 33 which is stopped in the light measuring position. Though not shown, the control section of the biochemical analysis system 1 which controls the overall operation of the system 1 is provided with a bar code reader and bar codes representing information on the item to be analyzed of the dry analysis element 11 to be inserted into each element chamber 33 is read by the bar code reader. The information on the item to be analyzed of the dry analysis element 11 to be inserted is stored together with the element chamber 33 in which the dry analysis element 11 is inserted.

The correction means 43 is further provided with a calibrating section 47 inserts a calibration element whose optical density is known into each of the element chambers 33 of the incubator rotor 30, receives the optical density of the calibration element as measured by the light measuring head 41 from the operating section 42 and writes the correction value for the element chamber on the basis of the difference between the known optical density of the calibration element and the measured optical density of the same in the memory 46.

The operating section 42 outputs corrected optical density to a concentration calculating section 48 and the concentration calculating section 48 determines the concentration of the component to be analyzed on the basis of the corrected optical density according to a calibration curve 49 and outputs the concentration of the component thus determined as a measured concentration.

Basic properties of the correction will be described with reference to FIGS. 4 and 5, hereinbelow. The sensitivity of the light measuring head 41 changes with change in distance d to the dry analysis element 11 generally as shown in FIG. 4. When a calibration element of a highly reflective ceramic whose optical density is known is measured, the output of the light measuring head 41 is maximized (Vo) at a point D at which the distance d is optimal, and is reduced as the distance d is reduced or increased. For example, at point a, where the distance d is smaller than at the point D, the output of the light measuring head 41 is reduced to V1 and at point b, where the distance d is smaller than at the point D, the output of the light measuring head 41 is reduced to V2. This properties changes in proportion with change of the optical density of the dry analysis element 11. On the basis of this fact, the correction value is set.

Figure 5:
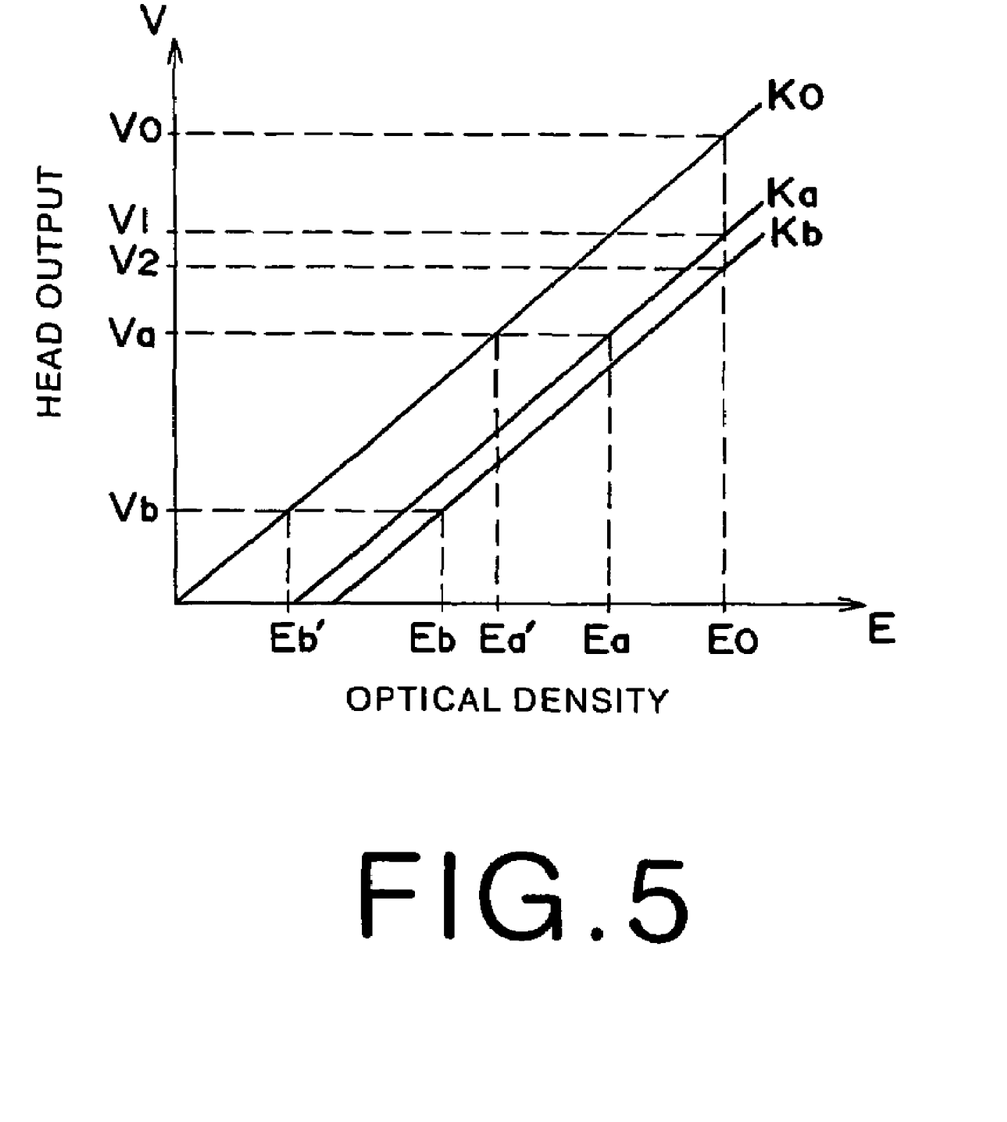
FIG. 5 is a view showing correction value properties.

FIG. 5 shows the relation between the output of the light measuring head 41 before correction and the corrected optical density. In FIG. 5, Ko is a line of correlation between the measured optical density Vo (the output of the light measuring head 41) as measured at the point D and the true optical density Eo. The correction value is set according to, for instance, correlation lines Ka and Kb (which are for the points a and b, respectively) which are obtained by moving parallel the line Ko so that the outputs V1 and V2 of the light measuring head 41 as measured at the points a and b correspond to the true optical density Eo.

That is, an output Va of the light measuring head 41 as measured at a distance from an element chamber 33 equal to that of the point a is converted according to the correlation line Ka to an optical density Ea which is higher than uncorrected optical density Ea' converted according to the correlation line Ko. Similarly, an output Vb of the light measuring head 41 as measured at a distance from an element chamber 33 equal to that of the point b is converted according to the correlation line Kb to an optical density Eb which is higher than uncorrected optical density Eb' converted according to the correlation line Ko.

The distance by which the correlation line Ko is moved to obtain the correlation line Ka or Kb is a function of the distance d between the light measuring head 41 and the element chamber 33 which can be represented by the rotating angle of the incubator rotor 30. Accordingly, by measuring a calibration element whose optical density is known and determining the deviation of the measured optical density from the known optical density as a distance from the optimal distance where the sensitivity of the light measuring head 41 is maximized, the influence on the measured value of fluctuation of the distance between the light measuring head 41 and the element chamber 33 can be compensated for.

For example, incubator rotors 30 have different rotational displacement properties due to, for instance, processing accuracy and the distance to the light measuring head 41 differs from element chamber to element chamber (in the light measuring position). A calibration element whose optical density is known is inserted into each of the element chambers 33 and the optical density of the calibration element in each element chamber 33 is measured while rotating the incubator rotor 30 to bring the element chambers 33 to the light measuring position in sequence. The correction value is determined for each element chamber 33 on the basis of the difference between the measured optical density and the known optical density, and the correction values for the respective element chambers 33 are stored together with the angular positions of the incubator rotor 30, i.e., the positions of the respective element chambers 33. Then the output of the light measuring head 41 is corrected (the measured optical density is corrected) on the basis of the correction value specific to the element chamber 33.

In FIG. 1, the sample tray 2 comprises a turntable 21 which is rotated in opposite directions. Five sample cartridges 7 are mounted on the turn table 21 in an arcuate line. The sample cartridges 7 are removable separately from each other. Each sample cartridge 7 comprises a sample holding portion 71 which holds a sample container 10 (a blood-collecting tube) holding therein a sample, and an analysis element holding portion 72 which holds a stack of virgin dry analysis elements 11 of different types.

Consumables are held on the other part of the upper surface of the turntable 21 along the outer periphery. For example, a number of nozzle tips 21, a mixing cup 13 (a molded product provided with a plurality of cup-like recesses), a diluent container 14 and a container 15 for other purposes are held on the turntable 21 along the outer periphery thereof. The consumables may be set on the sample tray 2 in the form of cartridges like the sample cartridge 7.

The turntable 21 of the sample tray 2 is rotated in the regular direction or the reverse direction by a drive mechanism (not shown) to positions where the spotting nozzle unit 5 operates. By controlling the angular position of the turntable and the position of the spotting nozzle unit 5, predetermined operations required to spotting the sample on the analysis element such as mounting a nozzle tip 12, sucking a sample, diluent or the reference liquid, and mixing the sample and the diluent are carried out.

An element transfer means (not shown) which transfers the dry analysis element 11 is provided at the central portion of the sample tray 2. The element transfer means comprises an element transfer member (an insertion lever) which is slid back and forth in a radial direction of the sample tray 2 by a drive mechanism (not shown). The element transfer means causes the element transfer member to push a dry analysis element 11 out of a sample cartridge 7 into the spotting station, to push the element 11 spotted with the sample into the incubator 3, and to further push the element 11 toward the center of the incubator 3 after measurement to discard the element 11. The element transfer means controls the drive mechanism for the turntable 21 to bring the sample cartridges 7 to the spotting station in sequence. When plasma of the sample is to be filtered, a holder 16 with a filter is mounted on the sample container 10 set in the sample cartridge 7 as shown in FIG. 1.

The dry analysis element 11 generally comprises a square mount and a reagent layer provided in the mount. A spotting hole is formed on the surface of the mount and the sample is spotted in the spotting hole. The dry analysis element 11 is provided with bar codes (not shown) representing information on the item to be analyzed.

The spotting station (not shown) is for spotting a sample such as plasma, whole blood, serum, urine or the like on the dry analysis element 11. Though not shown, a bar code reader for reading the bar code on the element 11 is provided on the upstream side of the spotting station. The bar code reader is for identifying the item of measurement and controlling the subsequent spotting and measurement, and for detecting the position of the element 11 (whether the element 11 is upside down or in a wrong direction).

The spotting nozzle unit 5 comprises a horizontal movement block 51 which is movable in a horizontal direction and a pair of vertical movement blocks 52 which are movable up and down on the horizontal movement block 51. A spotting nozzle 53 is fixed on each of the vertical movement block 52. The horizontal movement block 51 and the vertical movement blocks 52 are moved in the respective direction by drive means (not shown). The spotting nozzles 53 are integrally moved right and left and are moved up and down independently of each other. For example, one of the spotting nozzles 53 is for spotting the sample, and the other is for spotting the diluent.

The spotting nozzle 53 is in the form of a rod provided with an air passage extending in the axial direction and a pipette-like nozzle tip 12 is fitted on the lower end portion thereof. The spotting nozzles 53 are connected to air tubes respectively connected to syringe pumps (not shown), and a suction force and a discharge force are selectively supplied to the spotting nozzles 53. After measurement, the used nozzle tips 12 are removed from the spotting nozzles 53 and discarded.

The blood filtering unit 6 is inserted into the sample container 10 held in the sample tray 2 and sucks plasma through the holder 16 with a glass fiber filter which is mounted on the upper end of the sample container 10, thereby separating plasma from the blood and holding the separated plasma in a cup formed on the top of the holder 16. The blood filtering unit 6 comprises a sucking mechanism 61 which supplies suction force, and a suction pad 62 which is connected to a suction pump (not shown) and attracts the holder 16 under a suction force is provided on the lower end of the sucking mechanism 61. The sucking mechanism 61 is mounted on a support post 63 to be moved up and down by a drive mechanism (not shown). When the plasma is separated from the blood, the sucking mechanism 61 is moved downward to be brought into a close contact with the holder 16. In this state, the suction pump is operated to suck the whole blood in the sample container 10, whereby the plasma separated from the blood is introduced into the cup formed on the top of the holder 16. Thereafter, the sucking mechanism 61 is returned to the initial position.

In FIG. 1, a control panel 18 is provided above the incubator 3. The sample tray 2 and the spotting nozzle unit 5 are covered with a transparent protective lid 19 which is openable.

Operation of the biochemical analysis system 1 will be described, hereinbelow. A sample container 10 and one or more unsealed dry analysis elements 11 suitable for the item of measurement are set in a sample cartridge 7 outside the system body 17. Then the lid 19 is opened and the sample cartridge 7 is set in the sample tray 2. When a plurality of samples are to be measured, a plurality of suitable sample cartridges 7 are set in the sample tray 2. Further consumables such as the nozzle tips 12, the mixing cups 13, the diluent containers 14 and the like are set in the sample tray 2.

Then analysis is started. In case of emergency, analysis is interrupted and the sample cartridge 7 to be analyzed urgently is set in a vacant space or in place of another sample cartridge.

Blood plasma is first separated from the whole blood in the sample container 10 by the blood filtering unit 6. Then the sample tray 2 is rotated to bring the sample cartridge 7 containing therein a sample to be analyzed to the spotting station. Then one of the dry analysis elements 11 in the sample cartridge 7 is transferred to the spotting station by the element transfer member 91 of the transfer means 9. On the way to the spotting station, the bar code on the element 11 is read by the bar code reader and the item of analysis and the like are detected.

When the item of analysis represented by the bar code is colorimetry, the sample tray 2 is rotated to bring a nozzle tip 12 below the spotting nozzle 53 and the nozzle tip 12 is mounted on the spotting nozzle 53. Then the sample container 10 is moved and the spotting nozzle 53 is moved downward to dip the nozzle tip 12 into the sample and to cause the nozzle tip 12 to suck the sample. Thereafter the spotting nozzle 53 is moved to the spotting station and spots the sample onto the dry analysis element 11 at the spotting station.

Then the dry analysis element 11 spotted with the sample is inserted into an element chamber 33 of the incubator 3. In response to insertion of the dry analysis element 11 into the element chamber 33, the pressing member 34 presses downward the dry analysis element 11, whereby evaporation of the sample is prevented and the dry analysis element 11 is heated to a predetermined temperature. After insertion of the dry analysis element 11 into the element chamber 33, the incubator rotor 30 is rotated to bring the element chambers 33 to the measuring position in sequence where the dry analysis element 11 in the chamber 33 is opposed to the light measuring head 41. After a predetermined time, change of the optical density of the element 11 due to reaction of the sample with the reagent is measured by the light measuring head 41. After the measurement, the dry analysis element 11 is pushed toward the center by the element transfer member 91 to be discarded. The result of the measurement is output and the used nozzle tip 12 is removed from the spotting nozzle 53. Then processing is ended.

When the sample is to be diluted, e.g., when the blood is too thick to carry out accurate measurement, the sample tray 2 is moved to bring the nozzle tip 12 holding the sample to a mixing cup 13. Then the spotting nozzle 53 discharges the sample held by the nozzle tip 12 into the mixing cup 13. Then the used nozzle tip 12 is removed from the spotting nozzle 53, and a new nozzle tip 12 is mounted on the spotting nozzle 53. The spotting nozzle 53 causes the nozzle tip 12 to suck the diluent from the diluent container 14 and to discharge the diluent into the mixing cup 13. Thereafter the spotting nozzle 53 dips the nozzle tip 12 into the mixing cup and causes the nozzle tip 12 to repeat suck and discharge, thereby stirring the mixture in the mixing cup 13. Then the spotting nozzle 53 causes the nozzle tip 12 to suck the diluted sample and moves the nozzle tip 12 to the spotting station. At the spotting station, the spotting nozzle 53 causes the nozzle tip 12 to spot the diluted sample onto the dry analysis element 11. Then the aforesaid, light measuring step, element discarding step and result outputting step follow.

In the incubator of this embodiment, since the measured optical density output by the light measuring head 41 is corrected according to the position of the element chamber 33, that is, the distance to the light measuring head 41 of the element chamber 33, fluctuation of the distance between the light measuring head 41 and the element chamber 33 due to errors and/or strain in processing and/or assembly can be compensated for, and accordingly, the optical density of the dry analysis element 11 can be accurately measured without adding to the manufacturing cost of the incubator.

Figure 6:
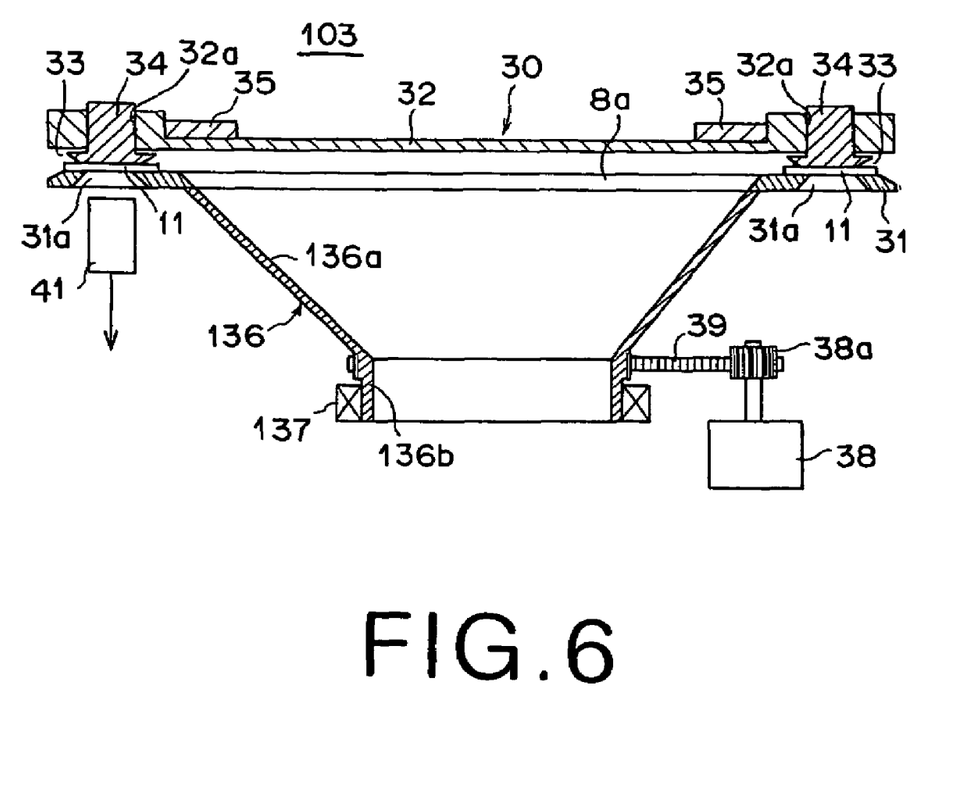
FIG. 6 is a cross-sectional view showing an incubator in accordance with another embodiment of the present invention.

FIG. 6 is a cross-sectional view showing an incubator in accordance with another embodiment of the present invention. The elements analogous to those shown in FIGS. 1 and 2 are given the same reference numerals and will not be described in detail here.

The incubator 103 of this embodiment comprises an incubator rotor 30 and a measuring means 4. The incubator rotor 30 comprises lower and upper disc members 31 and 32, and a plurality of element chambers 33 in which the dry analysis elements 11 are inserted are formed between the lower and upper disc members 31 and 32 arranged along the circumference of the disc members 31 and 32 at regular intervals. The bottom surface of each element chamber 33 is flush with the upper surface of the spotting station and the dry analysis element 11 can be inserted into the chamber 33 from the spotting station by simply pushing the element 11.

Sliding holes 32a are formed in the upper disc member 32 to be opposed to the element chambers 33. A pressing member 34 is disposed above each element chamber 33 with its upper portion slidably received in the sliding hole 32a. The lower surface of the pressing member 34 presses downward the dry analysis element 11 inserted into the element chamber 33 and tightly closes the spotting hole of the dry analysis element 11 (through which the sample is spotted onto the element 11) to prevent evaporation thereof. The outer edge of the lower portion of the pressing member 34 is tapered so that the dry analysis element 11 inserted into the element chamber 33 is brought into abutment against the tapered surface to push upward the pressing member 34.

A heater 35 is provided in the upper disc member 32 to heat the dry analysis elements 11 in the element chambers 33. By controlling the heater 36, the dry analysis elements can be held at a desired constant temperature (incubated).

A light measuring window 31a is formed in the bottom of the lower disc member 31 opposed to each of the element chambers 33. A light measuring head 41 is positioned below the light measuring window 31a of the element chamber 33 stopped in a light measuring position shown in FIG. 2. A circular opening 108a which opens in the element discarding hole to be described later is formed in the central portion of the lower disc member 31. A lower member 136 is provided below the circular opening 108a.

The lower member 136 is provided with a cone-like slant surface 136a which tapers downward toward the axis of rotation of the incubator rotor 30, a cylindrical rotating shaft 136b which is connected to the lower end of the slant surface 136a and the inner space of which opens to the space defined by the cone-like slant surface 136a so that the dry analysis element in each element chamber can be discarded outside the incubator 3 through the space defined by the cone-like slant surface 136a and the inner space of the cylindrical rotating shaft 136b.

A bearing member 137 horizontally supports the cylindrical rotating shaft 136b for rotation about the axis of rotation of the incubator rotor 30. When the slant surface 136a is at an angle not smaller than 30° to the horizontal, the dry analysis element 11 is surely slid on the slant surface 136a toward the cylindrical rotating shaft 136b.

In the incubator of this arrangement, the rotating shaft 136b need not be large in diameter even if the number of the dry analysis elements 11 to be accommodated in the incubator 3 increases and the diameter of the incubator rotor 30 increases, and accordingly, the bearing member 137 maybe small in diameter, whereby the incubator 3 can be manufactured at low cost. Further, since the dry analysis elements 11 after measurement can be discarded by pushing the dry analysis elements 11 only to the slant surface 136a, the stroke of the element transfer member need not be enlarged even if the number of the dry analysis elements 11 to be accommodated in the incubator 3 increases and the diameter of the incubator rotor 30 increases, whereby the incubator 3 can be small in size and weight.

Further by virtue of the lower member 136 defining the cone-like slant surface 136a, rigidity of the incubator rotor 30 is increased and the incubator rotor 30 can be rigid enough though it is small in weight, whereby wobbling of the incubator rotor 30 can be suppressed without use of a sliding support and the measuring accuracy can be enhanced.

What is claimed is:

1. An incubator comprising a rotating incubator rotor provided with a plurality of element chambers which are arranged along the outer periphery of the incubator rotor and each of which accommodates a dry analysis element spotted with a sample and incubates the dry analysis element, wherein the improvement comprises that the incubator rotor is provided with a cone-like slant surface which is formed below the element chambers and tapers downward toward the axis of rotation of the incubator rotor, a cylindrical rotating shaft which is connected to the lower end of the slant surface and an inner space of which opens to the space defined by the cone-like slant surface so that the dry analysis element in each element chamber can be discarded outside the incubator through a space defined by the cone-like slant surface and the inner space of the cylindrical rotating shaft, and a bearing member which supports the cylindrical rotating shaft for rotation about the axis of rotation of the incubator rotor.

2. An incubator as defined in claim 1 in which the slant surface is at an angle not smaller than 30° to the horizontal.

* * * * *